United States Patent [19]

Aebischer et al.

[11] Patent Number: 5,418,154

[45] Date of Patent: May 23, 1995

[54] METHOD OF PREPARING ELONGATED SEAMLESS CAPSULES CONTAINING BIOLOGICAL MATERIAL

[75] Inventors: Patrick Aebischer, Barrington; John F. Mills, Wakefield; Lars Wahlberg, Providence, all of R.I.; Edward J. Doherty, Mansfield, Mass.; Patrick A. Tresco, Salt Lake City, Utah

[73] Assignee: Brown University Research Foundation, Providence, R.I.

[21] Appl. No.: 997,770

[22] Filed: Dec. 24, 1992

Related U.S. Application Data

[63] Continuation-in-part of Ser. No. 722,852, Jun. 28, 1991, abandoned, which is a continuation-in-part of Ser. No. 638,759, Jan. 8, 1991, Pat. No. 5,283,187, which is a continuation-in-part of Ser. No. 461,999, Jan. 8, 1990, Pat. No. 5,158,881, which is a continuation-in-part of Ser. No. 121,626, Nov. 17, 1987, Pat. No. 4,892,538.

[51] Int. Cl.⁶ .................. C12N 11/04; C12N 5/00; B01J 13/02; A61K 9/48
[52] U.S. Cl. .................. 435/182; 264/4; 264/4.7; 424/451; 425/382 R; 425/382.2; 435/178; 435/179; 435/240.22; 435/240.23; 530/817
[58] Field of Search ............... 435/178, 179, 180, 182, 435/240.22, 240.23; 264/4, 417; 425/382 R, 382.2; 424/451; 530/817

[56] References Cited

U.S. PATENT DOCUMENTS

| 3,093,831 | 6/1963 | Jordan | 3/1 |
|---|---|---|---|
| 3,715,277 | 2/1973 | Dinelli et al. | 195/63 |

(List continued on next page.)

FOREIGN PATENT DOCUMENTS

| 0116311 | 8/1984 | European Pat. Off. . |
|---|---|---|
| 0147939 | 7/1985 | European Pat. Off. . |
| 0161640 | 11/1985 | European Pat. Off. . |
| 0188309 | 7/1986 | European Pat. Off. . |
| 0213908 | 11/1987 | European Pat. Off. . |
| 0363125 | 10/1989 | European Pat. Off. . |
| 2201129 | 4/1974 | France . |
| 2336176 | 7/1977 | France . |
| 2564734 | 11/1985 | France . |
| 2599639 | 12/1987 | France . |
| 2189809 | 11/1987 | United Kingdom . |
| 2192171 | 1/1988 | United Kingdom . |
| WO87/04367 | 7/1987 | WIPO . |
| WO89/04655 | 6/1989 | WIPO . |

OTHER PUBLICATIONS

Aebisher et al. (1991) Biomaterials 12:50–56.
Aebisher et al. (1991) Brain Research 448:364–368.
Aebisher et al. (1991) Brain Research 560:43–49.
Aebisher et al. (1991) Experimental Neurology 111:269–275.
Aebisher et al. (1991) J. Biomec. Engineering 113:178–183.
Aebisher et al. (1991) Science 242:133.
Chang (1977) Biomedical Applications Of Immobilized Enzymes and Protein, Plenum Press, N.Y., 1:69–90.
Hoffman et al. (1990) Experimental Neurology 110:39–44.

(List continued on next page.)

*Primary Examiner*—David M. Naff
*Attorney, Agent, or Firm*—Fish & Neave; James F. Haley, Jr.; Ivor R. Elrifi

[57] ABSTRACT

Elongated seamless capsules containing biological material are prepared by a method in which a coagulant, which includes a cell suspension or other biologically active factor, and a polymeric casting solution are extruded through a common extrusion port having at least two concentric bores, such that the coagulant is extruded through the inner bore and the polymeric casting solution is extruded through the outer bore. The method involves initiating extrusion of the coagulant subsequent to initiating delivery of the casting solution through the respective bores to form a capsule having a curved and smooth leading edge shape. Delivery of the coagulant is then shut off, and extrusion of the casting solution is terminated either immediately or after some predetermined time.

31 Claims, 8 Drawing Sheets

U.S. PATENT DOCUMENTS

| | | | |
|---|---|---|---|
| 3,821,087 | 6/1974 | Knazek et al. | 195/127 |
| 3,947,325 | 3/1976 | Dinelli et al. | 195/68 |
| 3,962,383 | 6/1976 | Hagiwara et al. | 264/4 |
| 4,163,691 | 9/1979 | Devos et al. | 435/174 |
| 4,241,187 | 12/1980 | White | 435/284 |
| 4,251,195 | 2/1981 | Suzuki et al. | 425/6 |
| 4,288,494 | 1/1981 | Porter et al. | 428/398 |
| 4,324,683 | 4/1982 | Lim et al. | 252/316 |
| 4,333,906 | 6/1982 | Porter et al. | 264/40.3 |
| 4,352,883 | 10/1982 | Lim | 435/178 |
| 4,353,888 | 10/1982 | Sefton | 424/25 |
| 4,378,016 | 3/1983 | Loeb | 128/260 |
| 4,391,909 | 7/1983 | Lim | 435/178 |
| 4,402,694 | 9/1983 | Ash et al. | 604/891 |
| 4,409,331 | 10/1983 | Lim | 435/178 |
| 4,426,337 | 1/1984 | Suzuki et al. | 264/4 |
| 4,451,253 | 5/1984 | Harman | 604/60 |
| 4,495,288 | 1/1985 | Jarvis, Jr. et al. | 435/241 |
| 4,686,098 | 8/1987 | Kopchick et al. | 424/424 |
| 4,695,466 | 9/1987 | Morishita et al. | 424/454 |
| 4,892,538 | 1/1990 | Aebisher et al. | 604/891.1 |
| 4,902,295 | 2/1990 | Walthall et al. | 623/11 |
| 4,902,450 | 2/1990 | Morrison | 264/4 |
| 5,158,881 | 10/1992 | Aebischer et al. | 435/182 |

OTHER PUBLICATIONS

Jaeger et al. (1991) Brain Research 551:163–170.

Jaeger et al. (1990) Progress In Brain Research 82:41–46.

Schratter (1976) Methods In Cell Biology, Academic Press N.Y. 14:95–103.

Sefton et al. (1987) Biotechnology Bioengineering 29:1135–1143.

Sugamori et al. (1989) Trans. Am. Soc. Artificial Internal Organs 35:791–799.

Sun et al. (1977) Diabetes 26:1136–1139.

Tresco et al. (1992) ASAIO Journal 38:17–23.

Tze et al. (1976) Nature 264:466–467.

Winn et al. (1991) Experimental Neurology 113:322–329.

Winn et al. (1989) Experimental Neurology 105:244–250.

Winn et al. (1989) J. Biomed. Mater. Res. 23:31–44.

Amicon: VITAFIBER "Artificial Capillary Systems for Tissue Culture" Publication No. 4426.

METHOD OF PREPARING ELONGATED SEAMLESS CAPSULES CONTAINING BIOLOGICAL MATERIAL

CROSS-REFERENCE TO RELATED APPLICATIONS

This application is a continuation-in-part of U.S. patent application Ser. No. 07/722,852 filed Jun. 28, 1991, now abandoned, which was a continuation-in-part of U.S. patent application Ser. No. 07/638,759 filed Jan. 8, 1991, now U.S. Pat. No. 5,283,187, which was a continuation-in-part of U.S. patent application Ser. No. 07/461,999 filed Jan. 8, 1990, now U.S Pat. No. 5,158,881, which was a continuation in part of U.S. patent application Ser. No. 07/121,626, filed Nov. 17, 1987, now U.S. Pat. No. 4,892,538.

BACKGROUND OF THE INVENTION

The technical field of this invention concerns the extrusion of capsules suitable for encapsulation of biologically active factors and other compositions.

There is considerable interest at present in the biologically active products of living cells, including, for example, neurotransmitters, hormones, cytokines, nerve growth factors, angiogenesis factors, blood coagulation factors, lymphokines, enzymes and other therapeutic agents. There is also substantial interest in developing new methods and systems for producing such biological factors, as well as in delivering these factors to subjects for therapeutic purposes.

For example, Parkinson's disease is characterized by the degeneration of the dopaminergic nigrostriatal system. Striatal implantation of polymer rods which release sustained amounts of a neurotransmitter, dopamine, has been reported to alleviate experimental Parkinsonism in rodents, indicating that the release of dopamine alone in the proper target structure may be able to correct this functional deficiency.

Similarly, diabetes is a disease characterized by the degeneration of the pancreatic endocrine system with a resulting loss in the body's ability to produce insulin. Although diabetes can be controlled, to an extent, by daily injections of insulin, optimal treatment protocols must take into account the individual's disease state, as well as changes in a subject's metabolism from day-today. For these reasons, polymeric matrix delivery systems for insulin have not been particularly successful.

Many other diseases are, likewise, characterized by a deficiency in a critical biological factor that cannot easily be supplemented by injections or longer-term, controlled release therapies. Still other diseases while not characterized by substance deficiencies can be treated with biologically active moieties normally made and secreted by cells. Thus, trophic and growth factors may be used to prevent neurodegenerative conditions, such as Huntington's and Alzheimer's diseases.

In contrast to the limited capacity of a polymeric matrix drug release system, the encapsulation of living cells has been proposed as a means to provide a continuous supply of neurotransmitters, hormones and other biological factors. The encapsulation of such cells by a permselective membrane which permits diffusion of the biological factor may not only prohibit the escape of mitotically active cells, but also prevent host rejection in the case of cross species or allogenic transplantation.

A number of researchers have proposed the use of microcapsules, i.e., tiny spheres which encapsulate a microscopic droplet of a cell solution, for both therapeutic implantation purposes and large scale production of biological products. For instance, the microsphere cell capsules disclosed by Sefton et al. Biotechnology and Bioengineering 29:1135–1143 (1987) and Sugamori et al. Trans. Am. Soc. Artf. Intern. Organs 35:791–799 (1989) are produced using a polymer solution to encapsulate a cell suspension in an aqueous culture medium. The polymer solution is delivered through an annulus formed by two concentric needles, while the cell suspension is delivered via the inner needle. The cell suspension and polymer solution form droplets which are blown off the end of the needle by a coaxial air stream. Each droplet falls into a curing bath, in which polymerization of a microcapsule occurs. The morphology sought by Sefton et al. and Sugamori et al. is a microcapsule having an inner sphere of cell solution, concentric with an outer sphere of polymer. This morphology is established during the fall of the droplet from the needle to the curing bath, and is influenced by factors such as the polymer/solvent systems and the relative densities of the polymer solution and cell suspension. The polymer/solvent systems disclosed by Sefton et al. and Sugamori et al. are chosen such that polymer precipitation occurs slowly. In the techniques of Sefton et al. and Sugamori et al. the curing bath serves to extract the polymer solvent. This ensures that polymerization occurs in the bath and not at the extrusion bore. The prior art technique is specifically designed to permit time for the polymer to surround the core material before solidification.

However, there are a number of shortcomings to the microencapsulation approach. For example, the microcapsules can be extremely difficult to handle, including being difficult to retrieve after implantation. The types of encapsulating materials which can be used are constrained by the formation process to polymers which can dissolve in biocompatible solvents. Furthermore, due to the limited diffusional surface area per unit volume of larger size spheres, only a limited amount of tissue can be loaded into a single microcapsule.

An alternative approach has been macroencapsulation, which typically involves loading cells into hollow fibers and then sealing the extremities. In contrast to microcapsules, macrocapsules offer the advantage of easy retrievability, an important feature in therapeutic implants, especially neural implants. However, the construction of macrocapsules in the past has often been tedious and labor intensive. Moreover, due to unreliable closure, conventional methods of macroencapsulation have provided inconsistent results.

In addition, existing techniques often produce macrocapsules with seams. This is due to the fact that an open end of the macrocapsule necessarily results from the macroencapsulation methods. For many applications, it is desirable to have a seamless capsule.

Thus, there exists a need for better techniques for macroencapsulation of cells for both therapeutic implantation and industrial production purposes. Encapsulation techniques which can be practiced in an automated fashion, which permit the usage of a wider range of materials, and which provide more reliable and/or seamless closure would satisfy a long felt need in the art.

SUMMARY OF THE INVENTION

Therapeutic agents, including living cells which produce biologically active factors, can be encapsulated within a semipermeable, polymeric membrane by co-extruding an inner coagulant stream and an outer polymeric casting solution through a common port to form a tubular extrudate having a polymeric membrane which encapsulates the cell suspension.

In one aspect of the invention, a method is disclosed in which a coagulant (which can include biological tissue fragments, organelles, or suspensions of cells and/or other therapeutic agents) and a polymeric casting solution are extruded through a common extrusion port having at least two concentric bores, such that the coagulant is extruded through the inner bore and the polymeric casting solution is extruded through the outer bore. The method involves initiating delivery of the coagulant subsequently to initiating extrusion of the casting solution through the respective bores (e.g., in a range of between about 10 milliseconds to about one second after initiating flow of the casting solution, or alternatively, after a drop of casting solution has been removed from the extrusion port). Delivery of the coagulant is then shut off, and extrusion of the casting solution is terminated either immediately or after some predetermined time. The timing of initiating extrusion of the casting solution relative to initiating delivery of the coagulant provides autoinitiation of the capsules and other extrudate formation.

In one embodiment, extrusion of the coagulant solution is stopped at intervals while maintaining extrusion of the casting solution to define separate compartments (e.g., cell culture chambers) connected by polymeric links. In another embodiment, a capsule is extruded that includes a tether formed from the polymeric extrudate integral with the capsule.

Strings of capsules, spheres and/or tethered capsules formed in this manner have a number of advantages over conventional, cell-encapsulating products. For implantable devices and other cell cultures, the multicompartment form ensures that breaks in the tubular membrane can be contained to individual cell capsules. Such cell capsules can thus be formed reliably without post-production processing. Moreover, the design is particularly advantageous in preparing implantable cell cultures for delivery of biologically active factors to a subject for therapeutic purposes. A string of cell capsules formed using the inventive method can be coiled, twisted, or otherwise deposited in various shapes to provide a dense and compact structure for implantation. Because the cell capsules are connected to each other, and/or include a tether, they can also readily be retrieved following implantation. The string-like nature of these products is particularly preferable over individual spherical microcapsules which typically are retrieved by aspiration, often resulting in a high percentage of unretrievable capsules and, consequently, inflammation in the subject.

Cell transport vehicles produced using the inventive method can be formed from a tubular extrudate by sealing the extrudate at intervals using various techniques. For example, the extrudate can be sealed by compressing it at intervals using mechanical or pneumatic force. Alternatively, the pressure under which the cell suspension or the polymeric solution is extruded can be modified to collapse the tubular extrudate at intervals and define separate cell compartments. In yet another technique, the flow of the cell suspension can be interrupted or otherwise impeded at intervals to likewise collapse the tubular extrudate and define cell compartments.

Tethered vehicles are also useful for delivery of biologically active factors to a treatment site. The tether may be attached outside the treatment site for later removal of the inserted, attached macrocapsule. Such vehicles may be formed from a tubular extrudate by continuing extrusion of the polymeric material through the outer bore following termination of delivery of the cell suspension.

The products of the present invention are particularly well-suited for use as therapeutic implant devices, such as those disclosed in U.S. Pat. No. 4,892,538, "In Vivo Delivery Of Neurotransmitters By Implanted, Encapsulated Cells" by Aebischer et al. issued Jan. 9, 1990, herein incorporated by reference. In U.S. Pat. No. 4,892,538, techniques are disclosed for implanting encapsulated neurotransmitter-secreting cells into a target region within a subject's brain, such that the encapsulated cells secrete a neurotransmitter and thereby permit constitutive delivery of a therapeutic agent to treat a neurological deficiency, such as Parkinson's disease. Alternatively, artificial organs capable of secreting other biological factors, such as hormones (e.g., insulin, thymic factors and the like) can also be constructed using the capsules, and/or multi-compartment cell capsule strings of the present invention.

Following extrusion, the polymeric solution preferably forms a semipermeable membrane upon coagulation. The membrane is a porous structure capable of protecting transplanted cells from autoimmune or viral assault, as well as from other detrimental agents in the external environment, while allowing essential nutrients, cellular waste products, and cell secretions to diffuse therethrough. As used herein, the term "selectively permeable" or "semipermeable" is used to describe biocompatible membranes which allow diffusion therethrough of solutes having a molecular weight up to about 150,000 (Mr).

The permeability of the polymeric membrane can be varied by controlling the viscosity of the polymeric casting solution, such that upon coagulation, the coating will form with a network of microchannels to provide diffusion pathways. In one embodiment, this can be achieved by employing a water-miscible solvent as a component of the polymeric solution and maintaining a pressure differential between the coagulant and the polymeric solution during extrusion. As the tubular extrudate forms, water from the coagulant infiltrates into the coagulating polymer to replace the solvent as the solvent is driven outward by the pressure difference. Upon coagulation, the water which has infiltrated into the polymeric membrane provides a network of pores. The optimal pressure and viscosity varies with the solvent and polymer employed, but can readily be ascertained for any particular polymer/solvent combination by those skilled in the art without undue experimentation.

In addition to the formation of capsular vehicles of various shapes (e.g., round or tubular) and provision for linked capsules (e.g., strings of capsules or tethered capsules), the present invention also permits significant control over the morphology of the capsule walls. For example, the pressure differential between the coagulant and the polymer casting supply can be varied to create larger pores (e.g. by increasing the pressure and- /or velocity of coagulant relative to the polymer casting supply). Moreover, two or more layers of different morphology (e.g. a tight-pored inner skin, or outer skin, or both) can be formed by either modulating the pressure/velocity of the co-extruded fluids, or by introducing external agents to influence coagulation of the outer surface.

In another aspect of the invention, a system is disclosed for encapsulating cells to produce the tubular extrudate and multi-compartment cell capsule products described above. This system can include a multiple annular extrusion port assembly (e.g., a spinneret or the like) having a first outer bore and a second, concentric inner bore, as well as a coagulant supply means for supplying the aqueous cell suspension to the inner bore of the extrusion head assembly, and a casting solution supply means for supplying the polymeric solution to the outer pore of the extrusion head assembly. As the cell suspension and polymeric solution are co-extruded, they form a tubular extrudate having a polymeric outer coating which encapsulates the cell suspension.

In one embodiment the method of the invention involves initiating extrusion of the casting solution, which may be a polymeric solution, through the outer bore of the extrusion port assembly. Shortly thereafter, typically within a time range of between about 10 milliseconds and about one second, delivery of the coagulant, e.g., a cell suspension to be encapsulated, is then initiated to the inner bore of the extrusion head assembly.

Alternatively, the casting solution flow is initiated, and allowed to continue until a drop of unpolymerized casting solution forms at the nozzle tip. In one embodiment, after the drop of unpolymerized casting solution falls or is otherwise removed from the nozzle tip, the coagulant flow is initiated (when an appropriate amount of casting solution has accumulated at the nozzle). If, when the unpolymerized drop is removed from the nozzle, an optional amount of casting solution remains, the coagulant flow is initiated immediately thereafter. In another embodiment, after the formation of the droplet at the nozzle tip, but before it falls away, coagulant flow is begun and the leading edge of the capsule is extruded. Contact of the coagulant with the casting solution causes the coagulation of the casting solution to begin. Before polymerization of the casting solution droplet at the leading edge can occur, it either falls or is removed so as to provide a curved and smooth leading edge to the capsule.

At a predetermined point in time after co-extrusion of the coagulant and casting solution has begun, delivery of the coagulant is terminated or interrupted. When the product is completed, delivery of the casting solution is then terminated. The method is preferably performed by extruding the casting solution through a smooth, non-porous (e.g., glass) bore, which results in formation of a smooth, seamless capsule. If extrusion of the casting solution is terminated some time after terminating delivery of the coagulant, the resulting capsule includes an integral tether. If delivery of the coagulant is interrupted, then continued, while continuously extruding the casting solution, the resulting vehicle is a string of capsules. Additionally, if the co-extrusion process is maintained for a sufficiently long period of time, sealed fibers containing a cell culture and/or other therapeutic agents can be formed automatically in a single step process.

The delivery of both the casting solution and the coagulant can be achieved using conventional pumps, such as infusion pumps commercially available from Harvard Apparatus Co., Natick, Mass. Alternatively, a pressure kettle system utilizing a pressurized fluid chamber can be used to pump fluid out of the fluid chamber through an output hose connected to the extrusion head assembly.

The system used in practicing the method may include rapid response time valves for controlling the delivery times of both the aqueous cell suspension and the casting solution during co-extrusion. In a preferred embodiment, the valves each have a 1 mm movement, and are able to move in the timing range of at least about 10 msec to about one second. In that system, the valves are air valves used in conjunction with an air pump system for a constant flow rate. The system may include valves positioned near or at the tip of the extrusion nozzles to enable precision timing of the casting and coagulant solution flows. These valves can be operated under computer control.

The system disclosed herein can include an aqueous quenchent bath for further coagulating the polymeric solution following extrusion, and/or various mechanisms for drying the tubular extrudate as it emerges from the extrusion head, including blowers, or evacuation chambers. The extrusion head assembly can incorporate additional bores to provide multiple coatings or to deliver a quenchent fluid about the tubular extrudate. The system can also include a sedimentation chamber for the cell suspension, or an equivalent cell packing mechanism, to increase the cell density within the aqueous cell suspension.

The invention will next be described in connection with certain illustrated embodiments; however, it should be clear that various additions, subtractions or modifications can be made by those skilled in the art without departing from the spirit or scope of the invention. For example, various aspects of this invention as applicable not only to the formation of sealed (or partially sealed) capsules but also to other extrudates, such as hollow fibers.

BRIEF DESCRIPTION OF THE DRAWINGS

Like reference characters in the respective figures indicate corresponding parts.

DETAILED DESCRIPTION

Figure 1:
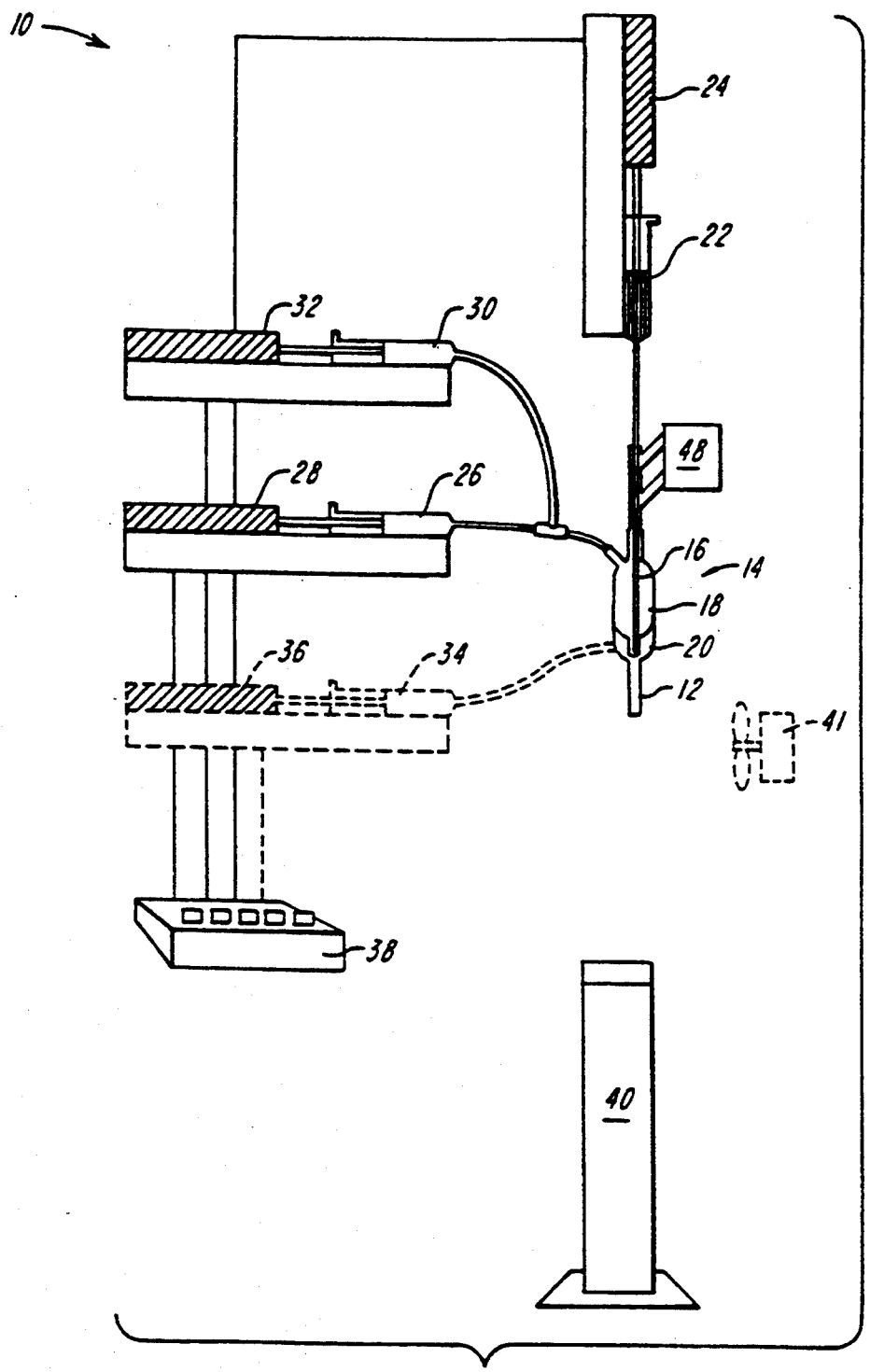
FIG. 1 is an overall schematic diagram of a system for encapsulating viable cells according to the invention.

In FIG. 1, a system 10 is shown for producing a tubular cell encapsulation vehicle 12 according to the method of the present invention, including an extrusion head 14 having a first (outer) bore 18, a second inner bore 16 and, optionally, a third (outermost) bore 20. The system 10 further includes a coagulant supply 22 and an associated pump 24, a casting solution supply 26 and an associated pump 28 and, optionally, a flush solution supply 30 with a pump 32. The pumps 24, 28 and 32 are preferably variable pressure (or variable flow rate) pumps, such that pressure differentials (e.g., between the coagulant and the polymer solution) can be established during use. In one embodiment, the pump can comprise a stepper motor with a shaft directed axially down the bore axis of a syringe, wherein the shaft drives a plunger down the bore of the syringe to create the flow of solution out of the syringe. Alternatively, instead of a stepper motor, the pump can comprise a gas-actuated piston connected to a plunger of a syringe. The piston pressure can be constant, or varied.

Additionally, the system can also, optionally, include an outer flowing quenchent supply 34 with an associated pump 36. All of the pump elements can be controlled manually or, preferably, by an automated controller (e.g., a microprocessor) 38. The system 10 can also include a quenchent bath 40, which would normally be disposed directly below the extrusion head 14 during operation. Alternatively, the system can include a blower 41 or the system can be employed within an evacuated or other reduced pressure chamber to aid in solvent removal.

Figure 2:
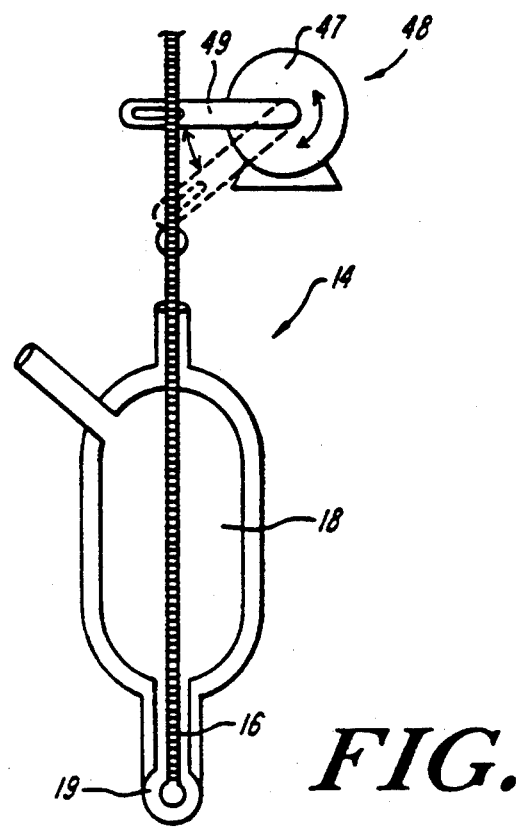
FIG. 2 is a more detailed schematic diagram of an extrusion head assembly for use in the system of FIG. 1.

In FIG. 2, the extrusion head 14 is shown in more detail, including an inner bore 16 for delivery of a coagulant and an outer bore 18 for delivery of a casting solution. The coagulant preferably includes a cell suspension, or other biologically active material to be encapsulated. The casting solution preferably is a polymer, and is alternately referred to herein as the polymeric solution. As the cell suspension and the polymeric solution are extruded through the common extrusion pore 19, the polymeric solution coagulates to form an outer coating about the cell suspension.

Figure 3:
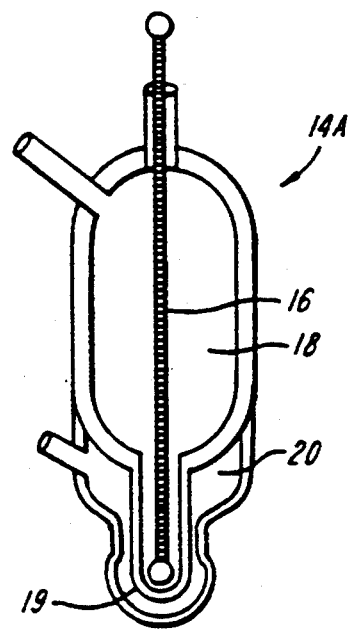
FIG. 3 is a schematic diagram of an alternative extrusion head assembly for use in the system of FIG. 1.

In FIG. 3, an alternative extrusion head 14A is shown in more detail comprising an inner bore 16 for the delivery of the cell suspension, a second, outer bore 18 (surrounding the inner bore) for delivery of the polymeric solution, and an outermost bore 20 for delivery of a flowing quenchent fluid, such as saline. In this embodiment, a smooth coating can be obtained by simultaneously extruding the cell suspension and polymeric casting solution through common bore 19 while applying a flowing quenchent fluid during the extrusion, e.g., from the outermost bore 20 in the extrusion head assembly 14A.

Figure 4A:
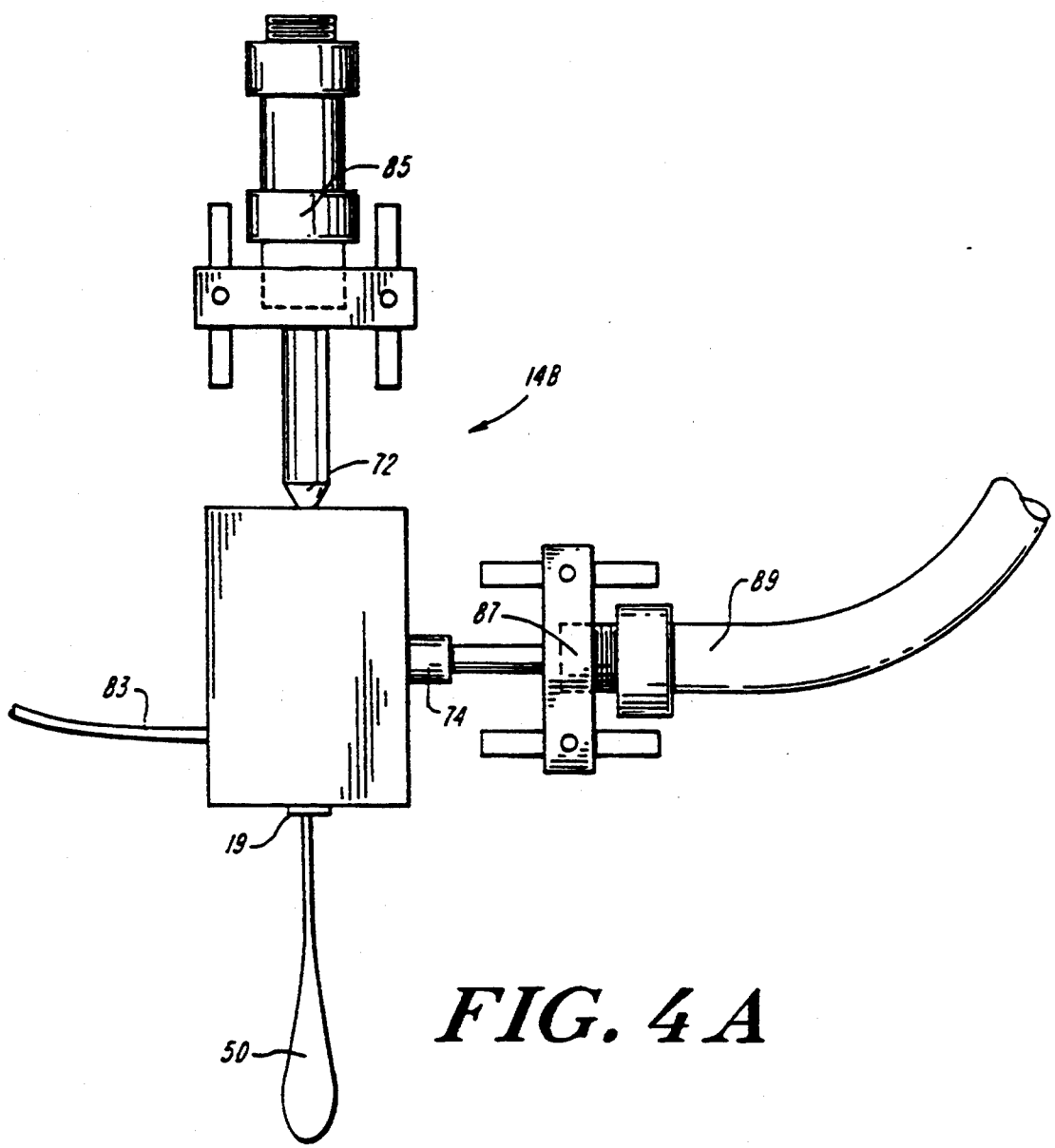
FIG. 4A is a schematic diagram of a valve assembly used in practicing the method of the present invention.
Figure 4B:
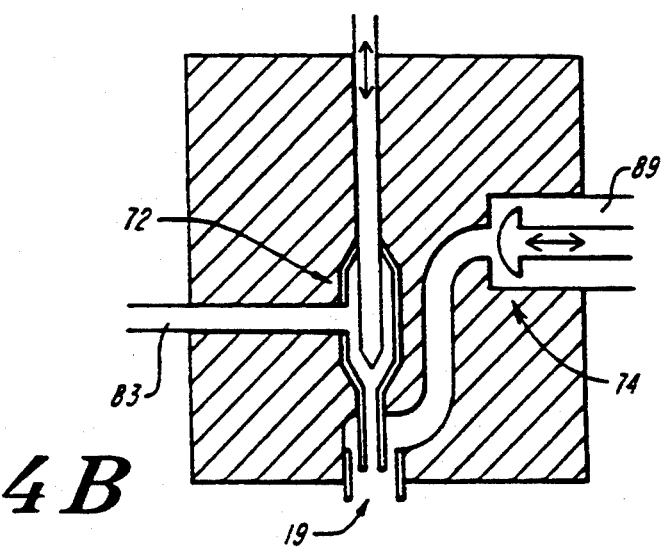
FIG. 4B is a partial cross-sectional view of the valve of FIG. 4A.

In FIGS. 4A and 4B another alternative extrusion head 14B is shown. FIG. 4A shows the overall extrusion head 14B which incorporates a needle value 72 activated by solenoid 85 for affecting the flow of the coagulant/cell suspension 83 and polymer valve 74 activated by solenoid 87 for affecting the flow of polymer casting solution 89. FIG. 4B is a partial cross-sectional view of the head assembly 14B in which the valves 72 and 74 are shown in more detail.

Figure 8A:
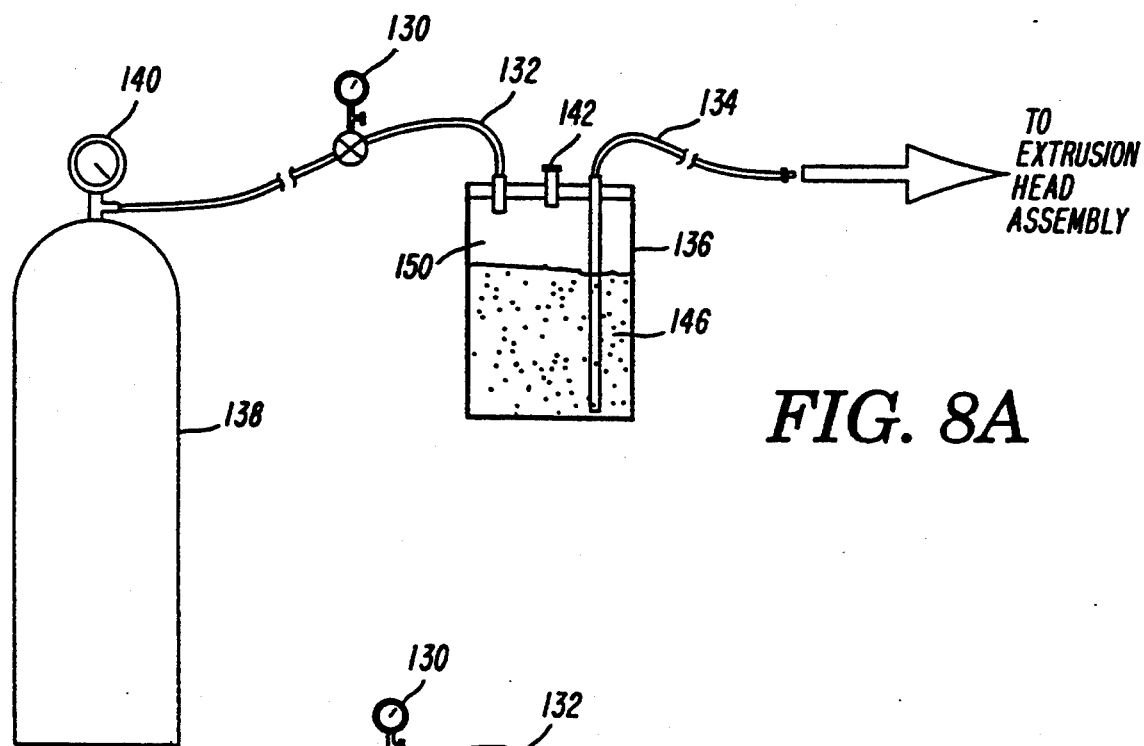
FIG. 8A is a schematic diagram of an alternate solution supply assembly.
Figure 8B:
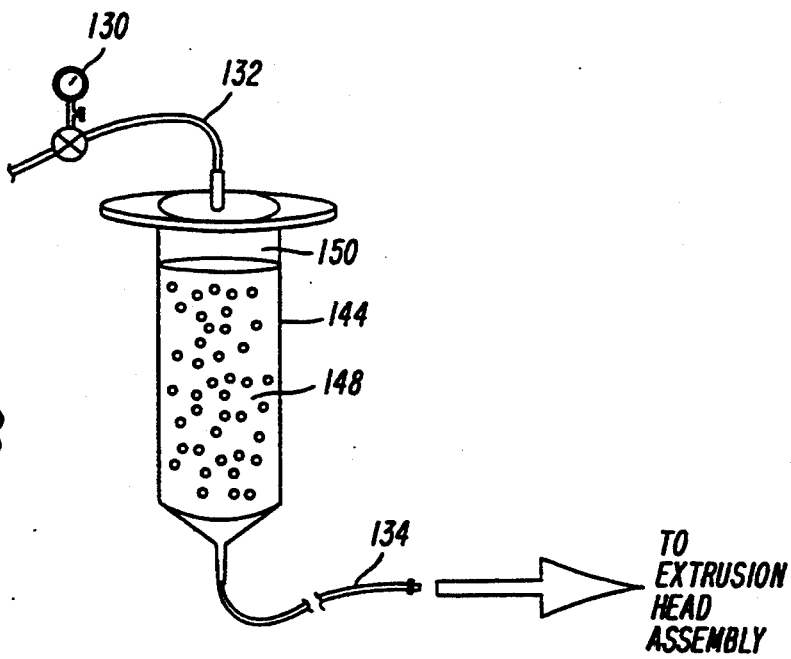
FIG. 8B is a schematic diagram of an alternate solution supply assembly.

FIGS. 8A and 8B show alternative casting solution supply and coagulant supply means. FIG. 8A illustrates an exemplary pressure kettle system for supplying a casting solution 146 to an extrusion head assembly, such as extrusion head 14 of FIG. 1, or 14B of FIGS. 4A and 4B.

Briefly, a pressure kettle 136 is coupled with a pressurized gas source 138 by a pressure hose 132, and coupled with an extrusion head assembly by output hose 134. Casting solution 146, disposed within kettle 136, can be "pumped" along the output hose 134 by pressurizing the kettle 136 through an infusion of gases from the gas source 138 into the air space 150 above the casting solution 146.

To control pressurization of kettle 136, one or more regulators can be disposed along the pressure hose 132. When highly compressed gases (i.e. >500 psi) are used, it may be desirable to employ a first stage regulator valve 140 to monitor the overall pressure of the gas source 138, and at least one second stage regulator valve 130 to more finely control the pressurization of kettle 136. Furthermore, kettle 136 may include a pressure relief valve 142, which, in addition to allowing equilibration of kettle 136 to atmospheric pressure, can also be employed to prevent over pressurization of the kettle 136. For instance, a relief valve 142 can be used which opens at kettle pressures in excess of a predetermined value.

Outflow of casting solution 146 from kettle 136 through output hose 134 can be controlled, for example, by solenoid actuated valves in the extrusion head assembly, such as illustrated in FIG. 4B, or by flow control valves (not shown) disposed in-line between kettle 136 and the extrusion head assembly.

FIG. 8B shows another embodiment of a pressure kettle system in which a coagulant solution 148 is disposed within a pressure kettle 144, shown here to be a syringe body. Pressure hose 132 couples the kettle 144 to a gas source 138, and output hose 134 directs a flow of coagulant solution 148 to an extrusion head assembly. Pressurization of the kettle 144 results in the flow of coagulant solution 148 through the output hose 134 to an extrusion head assembly.

The gas source 138 can be any pressurized source of gases compatible with the encapsulation of biological material, especially cells, as well as relatively inert with respect to reacting with the polymer/solvent system. An example of a preferred gas source is compressed nitrogen ($N_2$). In some instances, it may be desirable to dispose a filter between the gas source 138 and the pressure kettle 136 or 144 in order to prevent contamination of the solutions by agents such as microorganisms, and oils (e.g. from compression processing of the gases), or other particulate matter suspended in the gas flow. Filters useful to this end are well known in the art.

Where desirable, the regulator valves, pressure relief valves, and flow control valves can be monitored and operated by a microprocessor. Rapid control of flow rates may be controlled by flow control valves, and in some instances, by control of the relief valve. Slower control of flow rates can be accomplished by adjustments to the kettle pressure by the regulator valves, but, in the absence of any other perturbation to the system, will occur dependent on Boyle's law.

Figure 5A:
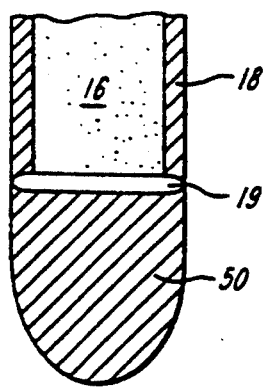
FIG. 5A is a schematic illustration of an initial stage of an extrusion technique according to the invention.
Figure 5B:
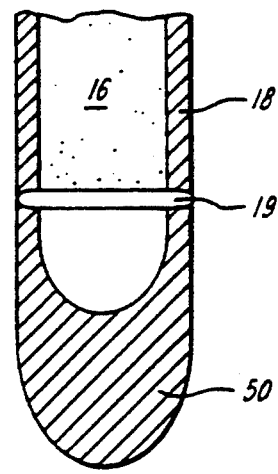
FIG. 5B is a schematic illustration of a subsequent stage in extrusion shown in FIG. 5A.
Figure 5C:
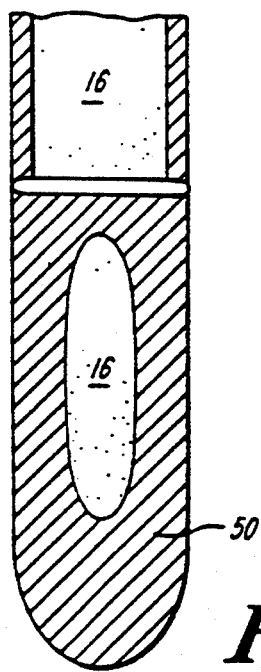
FIG. 5C is a schematic illustration of a further stage in the extrusion shown in FIG. 5B.

Referring now to FIGS. 5A through 5C, in practicing the method of the invention, polymer solution supply pump 28 or pressure kettle 136 is activated to initiate extrusion of the polymer solution to the first, outermost bore 18. By thus initiating flow, one end of the capsule is subsequently formed as a closed cap 50, as shown in FIG. 5A. For example, in one embodiment, within 10 milliseconds (msec) to about one second coagulant supply pump 24 is activated to initiate delivery of the coagulant to the second, innermost bore 16. The preferred range is between about 300 and 700 msec; typically approximately 500 msec. The exact timing depends on the type of polymer used as the casting solution, as well as the chosen flow rate of that casting solution. It should be noted that after initial operations, there may be sufficient residual polymer in the exit channel 11 and/or polymer reservoir 17 to allow the initiation of coagulant flow to be simultaneous or even precede the initiation of the polymer flow and still produce smooth capsules and/or fibers.

In another embodiment casting solution flow is initiated, but coagulant flow is not initiated until a drop of unpolymerized casting solution falls or is otherwise removed from the nozzle tip. Coagulant flow is then initiated. Under these circumstances, depending upon the casting solution flow rate, coagulant flow may not be initiated for a number of seconds after casting solution flow is begun. Relative to the accumulation of the optimal amount of casting flow within the nozzle tip, however, coagulant flow is initiated instantaneously. This particular technique is suitable both for the initiation of the first capsule, as well as for initiation extrusion of subsequent capsules.

The coagulant includes the biological, or other, material to be encapsulated. If the coagulant includes cells, the coagulant is a physiologically compatible aqueous solutions (e.g., saline), buffered saline, culture medium, or the like.

As shown in FIG. 5B, initiating flows of coagulant begins formation of a central tube of encapsulated material. The next step of the inventive method involves terminating (at least temporarily) the delivery of the coagulant. This results in a completely encapsulated aliquot of material, as shown in FIG. 5C. At this point, extrusion of the polymer casting solution may be terminated to form a single vehicle. As illustrated in FIGS. 6A-6E, and discussed in further detail below, different forms of cell transporting vehicles may be manufactured using the inventive method.

When the system 10 of FIG. 1 is employed to shape the tubular extrudate into a multi-compartment cell capsule string, a retraction means 48 can be employed to periodically retract the inner bore 16 so as to interrupt the flow of the cell suspension. This retraction means can take various forms. For example, the inner bore can slide along its longitudinal axis and be retracted by motor 47 and pivot arm 49 as shown schematically in FIG. 2. Alternatively, the retraction can be accomplished by eccentric cam elements, or a simple lever, or other means obvious to those skilled in the art. The effect of these retractions is to periodically seal the tubular extrudate and again form multiple compartments. In yet another alternative approach, the controller 38 (shown in FIG. 1) can vary the pressure or flow applied by pump 24 (and/or pump 28) to create periodic interruptions in the flow of the cell suspension.

In one form of practicing the present inventive method, a multiple annular spinneret may be used, similar to that used in forming hollow fibers. Using a spinneret, coupled with precisely timed coagulant flow, the method provides for 'autoinitiation' of extrusion without the need for mechanical assistance or spinning. Autoinitiation can be further facilitated, in some applications, by the use of non-porous or hydrophobic outer bore materials, such as glass, sapphire or Delrin. In "autoinitiation", the initiation of extrusion of the casting solution to the outer bore 18 automatically begins vehicle formation without nozzle clogging or rough-edge formation. This autoinitiation enables the endcaps 50 of the resulting vehicles to be smooth and seamless, and eliminates the need to manually initiate extrusion.

To produce a desired shape leading edge of a capsule, phase inversion (i.e., the contact of coagulant and casting solution as normally occurs at the onset of coagulant flow) must occur at an optimal time during nascent droplet formation of the casting solution on or in the extrusion nozzle. The optimal timing of coagulant onset will produce a leading edge of the incipient capsule which is curved and smooth. The timing can be precisely controlled to produce capsules that have ends that are bullet-shaped, bulbous (as the end of a dumbbell or a scallion), or a variety of other configurations, particularly if additional forces (beside gravity) are appropriately applied during extrusion. To insure the reproducible formation of a smooth leading edge, care must also be taken to avoid practices which lead to nozzle clogging during extrusion initiation (e.g., high ambient humidity).

Factors affecting casting solution droplet growth size and shape, on or in the extrusion nozzle, in the absence of coagulant include: nozzle geometry; flow rate of the casting solution; annulus size; annular geometry; inner bore size and geometry; wetting characteristics of nozzle material; and surface tension of the polymer.

Annulus size and wetting characteristics of the nozzle material define the size of drop that can be supported for a given polymer. In conjunction with nozzle geometry, flow rate defines the growth rate and the shape of the nascent droplet. Surface tension of the polymer will also influence the size and shape of the droplet, and the size droplet that can be supported. The following is a list of additional factors which may distort the nascent droplet to a geometry other than hemispherical (in some cases, one or more of these forces may actually be employed to produce a leading edge of a given geometry): positive pressure due to onset of coagulant flow; angle of the nozzle relative to gravity; vibration; application of vacuum to outside of the nozzle; the use of a static electricity source to distend the droplet; mechanical extraction of the nascent droplet (e.g., through the use of an appropriately positioned capillary tube beneath the nozzle, or by centrifical force, photo-induced shock waves, vibrations, electromotive force, or mechanical movement of the nozzle). The effects of any of these parameters may also be altered by changes in the relative viscosity of the casting or coagulant solution.

Once the desired shape droplet is achieved and the time to form the droplet for a given polymer flow rate is determined, additional considerations can be employed to insure appropriate autoinitiation and smooth capsule leading edge production. For most applications, the size of the drop of casting solution at the onset of coagulant flow is preferably so small as to have minimal outward curvature. If the drop is allowed to become larger than hemispherical (i.e., the angle of incidence to the annular lip is greater than 90°), bulbous end capsules will be produced. Any effects on droplet shape and size due to any increase in pressure caused by initiation of the coagulant flow can be anticipated and accounted for in determining the appropriate time after onset of casting solution flow to begin coagulant flow.

During the repetitive extrusion of capsules, termination of casting solution flow between sequential capsules should occur cleanly. Clean termination is important for the production of a properly-formed trailing edge of the extruded capsule, as well as controlled and predictable formation of the leading edge of the subsequent capsule. Clean termination refers to the termination of casting solution flow in such a fashion that when the extruded capsule falls away or is ejected, no unwanted or detrimental residual, unprecipitated or partially precipitated already-extruded casting solution remains attached to the nozzle. Such residual solution may potentially result in a detrimental shape or geometry of the subsequent capsule or causes nozzle clogging.

Clean termination disrupts the continuity between the unpolymerized polymer in the trailing edge of the extruded capsule and the polymer remaining in the extrusion nozzle. Such disruption assures that no detrimental shapes are produced in either the trailing edge of the extruded capsule or in the leading edge of the subsequent capsule. The following methods may be useful in producing clean termination: the rate of extrusion of the capsule can be adjusted; flow rates of polymer and/or coagulant can be increased resulting in a higher velocity of capsule extrusion; varying the velocity of the needle valve 72 during the closure stroke can be used to change the velocity of capsule extrusion independent of polymer or coagulant flow rates. Alternatively, the needle valve 72 can be constructed so that after sealing off the coagulant flow, the needle continues to move into the coagulant flow channel towards the channel lumen. In this way, the flow channel is purged of residual coagulant, and a force is provided to cleanly eject the extruded capsule. In other embodiments, an additional input with appropriate valves and pumps may be placed within either the solvent flow path or the coagulant flow path so that a purge slug of solvent, water, air, or an immiscible liquid, such as mineral oil, may be delivered between capsules. The additional input should be constructed so that the purge slug can be delivered precisely at the time of polymer flow termination. In some cases, an outermost third lumen on the extrusion nozzle may be employed to deliver a high flow rate frictional source (e.g., air) which will promote clean termination of capsule extrusion.

In other embodiments, in the instance of extrusion of a first capsule, or following completion of a first capsule, unwanted residual polymer within or on the nozzle is eliminated by initiating polymer flow in the absence of coagulant, until a droplet of unprecipitated casting solution falls from the nozzle. Onset of coagulant flow is timed with the drip of unpolymerized coagulant such that the resulting leading edge of the extruded capsule is formed from a minimal casting solution volume. The leading edge is not formed from the dripped casting solution.

In another embodiment, a mechanical blade or arm may be used to physically disrupt the continuity of casting solution between sequentially extruded capsules.

During coextrusion, internal pressure, i.e., pressure of the coagulant as it flows through the inner bore, is controlled to assure that solvent in the polymer casting solution is driven outward and, thereby, does not affect adversely the viability of the cell suspension. This transmembrane pressure (TMP) can be adjusted to achieve an optimal level which removes solvent from the casting solution without damaging cells in suspension. While the exact pressure depends on several variables, including nozzle size, flow rate, polymer and coagulant composition, empirical observations can be used to indicate when the desire TMP is achieved. In one preferred form of the invention, the appearance of tiny solvent beads on the outside of the extrudate approximately 5 mm from the tip of the nozzle indicate optimal TMP.

Controlling the flow rate is one method of controlling TMP. The flow rate of the coagulant preferably will range from about 0.8 to about 5.0 times the flow rate of the polymer solution. For example, using polyacrylonitrile/polyvinylchloride (PAN/PVC) as the polymer casting solution, a flow rate of 0.8 ml/minute PAN/PVC with a flow rate of 1.5 ml/minute coagulant can be used.

Typically, the above described process will result in an inner capsule or other extrudate surface that is relatively smooth (tight pored) and a thicker outer layer characterized by a network of interconnected pores on "trabeculae" which together provide a semipermeable ("permselective") membrane. In some instances, it may be preferable to also have an outer skin characterized by tight pores. The double skin extrudate offers a second layer of permselective protection. The addition of the outer layer can insure permselectivity control, potentially even in the presence of minor damage to the inner layer. Additionally, host cells do not have access to the inner trabeculae of the extrudate wall, which may be useful for some applications. The addition of the second skin also leads to a stronger extrudate. In these double skinned capsules, the trabecular layer is bounded on either side by permselective skins. The skins are generally on the order of 5-10 $\mu$m in thickness and have a molecular weight cutoff on the order of 40-60k. Nonsolvents can be added to the polymer to further regulate permselectivity.

Double skinned extrudates are prepared by limiting coagulant-induced precipitation of the casting solution to only the inner portions of the nascent extrudate. Before convective flow of coagulant solution can induce complete precipitation of the outermost portion of the extrudate wall, precipitation of the outer extrudate wall is induced from a separate external coagulant source. Examples of external precipitating sources include a precipitation bath into which the extruded extrudate is plunged immediately as it emerges from the nozzle, or a third lumen in the spinneret external to the polymer carrying bore. This lumen can be used to deliver an additional coagulant. A humidified atmosphere may also be used as an external coagulant to precipitate the outer wall region of the nascent extrudate as it emerges from the spinneret.

In order to insure that convective flow of the center bore coagulant does not induce precipitation of the outer portion of the nascent extrudate wall, the flow rate of coagulant through the inner bore should be reduced relative to casting solution flow. (e.g. to 0.6–1.0 times the casting solution for a nozzle of the dimensions 600 μm i.d.) Note that while the coagulant flow may be reduced relative to casting solution flow, the actual velocity of the coagulant flow (flow rate/unit area) is greater than the casting solution velocity. This leaves a net outward convective flow of coagulant. The net outward flow is important for maintaining extrudate permeability and ensuring rapid precipitation.

When an adjustable center bore plunger valve is employed in the extrusion nozzle, it is important that the stroke of the plunger doesn't lead to variation in coagulant flow during the extrusion of a single capsule. Such variation can sometimes lead to outer skin formation on only a part of the capsule. Thus to insure uniformity in the outer skin, it is important that the traverse of the center bore plunger be limited to the point where it just blocks coagulant flow. Continuing after the cessation of coagulant flow will tend to have an injection effect on the residual coagulant present in the center bore in front of the plunger. The injection effect increases the net outward convective flow of coagulant and under many circumstances will result in coagulant mediated precipitation of the entire fiber wall, eliminating the outer skin near the trailing edge of the capsule.

Various polymers can be used as the casting solution to form the membrane coatings of the present invention. Polymers may include ones derived from solutions which would otherwise be incompatible with the propagation of living cells. For example, polymeric membranes can be formed from polyacrylates (including acrylic copolymers), polyvinylidenes, polyvinyl chloride copolymers, polyurethanes, polyethylene oxide, polystyrenes, polyamides, cellulose acetates, cellulose nitrates, polysulfones, polyacrylonitriles, as well as derivatives, polymer blends, copolymers, and mixtures thereof.

The solvent for the polymer solution will depend upon the particular polymer chosen for the membrane material. Suitable solvents include a wide variety of organic solvents, such as alcohols and ketones, generally, as well as dimethylsulfoxide (DMSO), dimethylacetamide (DMA) and dimethylformamide (DMF), in particular. In general, water-miscible organic solvents are preferred.

Coagulant, polymer-solvent, polymer and any additives or copolymers, etc. should be chosen to produce a rapidly precipitating system. Precipitation must occur rapidly enough so that the cross-sectional shape of the nascent capsule will be preserved as it leaves the nozzle tip. This generally means that precipitation will begin almost instantaneously as the coagulant from the center bore meets the polymer within the nozzle tip. As long as the capsule morphology is maintained by the initial phases of the precipitation, the reaction does not necessarily have to be fully completed until the extruded capsule is fully free of the nozzle. In some cases, such as the preparation of a double skinned fiber, it is desirable to avoid precipitation of the outer region of the fiber wall by coagulant from the center bore. Components should be selected for which terniary phase diagrams can be constructed. Methods for selecting terniary phase components which display small miscibility gaps (e.g. PAN/PVC; $H_2O$; 13.5% DMSO) and resulting quick precipitation times are well known in the art.

The polymeric solution, or 'dope', can also include various additives, including surfactants to enhance the formation of porous channels, as well as antioxidants to sequester oxides that are formed during the coagulation process. Exemplary surfactants include Triton-X 100 available from Sigma Chemical Corp. and Pluronics P65, P32, and P18. Exemplary anti-oxidants include vitamin C (ascorbic acid) and vitamin E. Moreover, when the vehicles of the present invention are designed for implantation, materials such as anti-inflammatory agents, angiogenic factors, and cell growth factors, can also be incorporated into the polymeric membrane to reduce immune response or stimulate the cell culture, respectively. Exemplary anti-inflammatory agents include corticoids such as cortisone, dexamethasone, cortisol, interleukin-1 and its receptor antagonists, and antibodies to TGF-$\beta$, to interleukin-1, and to interferon-gamma. Exemplary angiogenic factors include fibroblast growth factor and nerve growth factor. Alternatively, these materials can be added to the multi-compartment cell capsule vehicles after formation by a post-coating or spraying process. For example, the vehicles can be immersed in a solution which contains an anti-inflammatory agent, such as a corticoid, an angiogenic factor, or a growth factor following extrusion to post-coat the cell capsules.

Post-coating procedures can also be used to provide a protective barrier against immunogens and the like. For example, after formation, the cell vehicles can be coated (e.g., by immersion, spraying or applying a flowing fluid during extrusion) with a surface protecting material, such as polyethylene oxide or polypropylene oxide (e.g., having a molecular weight of about 10,000 Daltons or greater), to inhibit protein interactions with the capsules.

Autoinitiation and the smoothness of the resulting encapsulation vehicle may be affected by the use of smooth, non-porous (e.g., glass or ceramic) bores. Similar results may be achieved using a material having surface and wetting characteristics similar to those of glass. While the use of glass is preferred in practicing the inventive method, bores made of other materials such as metals, (e.g., titanium or stainless steel) or high temperature resistant plastics (e.g., Teflon or PCV acetate) may be used in particular applications. For example, with reference to FIG. 1 again, the inner bore can be constructed of glass, sapphire, stainless steel, diamond, kevlar reinforced fiberglass, and surface modified plastics, metals or carbons in order to produce low surface tensions. For similar reasons, at least the outer surface, and mouth, of the outer bore should likewise have low surface tensions and can be constructed from materials such as glass or paraffin coated glass.

Virtually any length vehicle can be made by the instant invention. Although the lower limit is bounded by a requirement for a minimal fiber wall thickness at each end (e.g., 20 μm wall thickness at each end), the vehicle length can range from about 50 μm to several centimeters or more. In preferred embodiments, vehicle wall thickness is generally on the order of 50–100 μm. The cross-sectional area of the vehicle is primarily a function of the diameter of the nozzle orifice and will generally be greater than 50 μm$^2$. Typical diameters useful in the production of cell-containing vehicles are greater than 100 μm, generally on the order of 400–1,000 μm, preferably about 800 μm.

A 720 μm inner diameter (I.D.) outer bore spinneret can be used to produce an 800 μm outer diameter (O.D.) vehicle. In order to autoinitiate capsule extrusion from a spinneret of 720 μm diameter and produce an endcap wall of a minimum of 40 μm in thickness (endcap wall volume of approximately 20 μl), a volume of polymer of at least about 40 μl should be present in advance of the coagulant front (in most cases, this means extruded or "passed by the tip of the center bore" prior to initiating coagulant flow). Preferred polymer flow rates for this size nozzle range from about 0.2 ml/min to about 5 ml/min, preferably on the order of about 0.75 to 2 ml/min. For this range of flow rates, 40 μl of polymer will be extruded during the initiation period (e.g., from 100 msec to over 1 sec). These and similar timing calculations can be performed to determine the necessary delay before the onset of coagulant flow under various conditions. For larger or smaller diameter bore spinnerets, flow rates can be scaled and the timing adjusted accordingly.

In a preferred embodiment, the resulting extrudate has a length-to-diameter (L/D) ratio of between about 3:1 and about 5:1. Typically, the extrudate has a length of approximately 0.5 cm, with a preferred L/D ratio of at least about 5:1.

In other embodiments, where the leading edge is to be formed from polymer residue after a drip of unprecipitated polymer falls from the nozzle tip, the nozzle shape should be designed so that only the desired amount of unprecipitated polymer ("holdup volume") is present at the initiation of phase inversion. The use of a movable center bore for the delivery of coagulant allows adjustment of the total "dead space" present beneath the center bore. Other means to minimize the hold up volume of unprecipitated casting solution include the use of hydrophobic material on the outside and lip of the outer bore. Minimal lip thickness of the outer bore, and low viscosity casting solution also aid in minimizing holdup volume.

Various cell lines can be encapsulated according to the present invention. As noted above, the multi-compartment cell vehicles are particularly useful for the delivery of neurotransmitters, such as dopamine, or enkephalins which are secreted by cells of the adrenal medulla, embryonic ventral mesencephalic tissue and neuroblastic cell lines. PC12 cells (an immortalized cell line derived from a rat pheochromocytoma) are particularly preferred in some applications because of their ability to secrete large amounts of dopamine and other active factors over long periods of time. Other neurotransmitters include gamma aminobutyric acid (GABA), serotonin, acetylcholine, noradrenaline and other compounds necessary for normal nerve functions. A number of cell types are known or can be isolated which secrete these neurotransmitters. Cells can also be employed which synthesize and secrete agonists, analogs, derivatives or fragments of neurotransmitters which are active, including, for example, cells which secrete bromocriptine, a dopamine agonist, and cells which secrete L-dopa, a dopamine precursor.

In other embodiments of the invention, the encapsulated cells can be chosen for their secretion of hormones, cytokines, nerve growth factors, angiogenesis factors, antibodies, blood coagulation factors, lymphokines, enzymes, and other therapeutic agents. Other biologically active factors may include neurotransmitters, neuropeptides, and trophic factors. Exemplary neuropeptides include enkephalins, endorphins, dynorphins, and Substance P. Exemplary factors include nerve growth factor (NGF), platelet-derived growth factor (PDGF), epidermal growth factor (EGF), brain-derived neurotrophic factor (BDNF), neurotrophin-3 (NT-3), an array of fibroblast growth factors, and ciliary neurotrophic factor.

The aqueous cell suspensions can further include various additives to protect the cells during the extrusion process or to stimulate their growth subsequently. Such additives may include, for example, a nutrient medium or growth factors which are incorporated into the aqueous suspension, as well as an anchorage substrate material to enhance cell attachment. The anchorage substrate material can be a proteinaceous material, such as collagen, laminin, positively charged polyelectrolytes, or polyamino acids. Alternatively, the cell suspension or the polymeric solution (or both) can include a foaming agent or a blowing agent which can distort the inner surface of the polymeric coating to increase the anchorage surface area of the tubular interior.

The products of the present invention can take various forms, as illustrated in FIGS. 6A–6E, including simple tubular extrudates as well as multi-compartment cell capsule vehicles. The shape of the multi-compartment vehicles can be tubular, resembling sausages, or nearly spherical, resembling strings of pearls. The maximum outer diameter of the vehicle will typically range from about 0.1 to about 1.0 millimeters. The membrane wall thickness will typically range from about 50 to about 200 micrometers. The membrane porosity may be controlled to effectively keep high molecular weight complement components (e.g., C1q) and other cells from flowing into the extruded capsule, while enabling the encapsulated materials to flow out into the target site. Thus, the molecular weight cut-off is preferably in the range of 50 to 150 kd. The length of the vehicles will vary depending upon the particular application and specific embodiment.

Figure 6A:
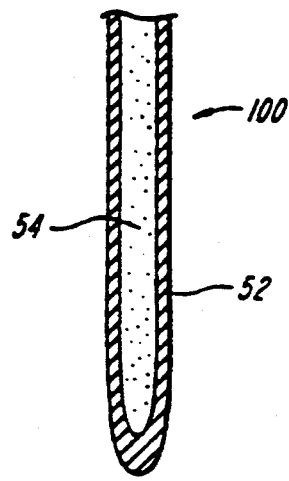
FIG. 6A is a schematic cross-sectional view of an encapsulation vehicle formed according to the invention.
Figure 6B:
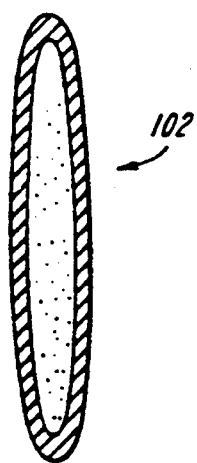
FIG. 6B is a schematic cross-sectional view of another encapsulation vehicle formed according to the invention.

FIG. 6A illustrates the end portion of an exemplary vehicle 100 manufactured using the inventive method. The vehicle 100 generally includes an outer membrane 52, which may be coated with a biocompatible material, and an inner chamber 54 containing the biological material, or other material. FIG. 6B illustrates a single-aliquot type vehicle 102, manufactured in accordance with the inventive method as described above.

Figure 6C:
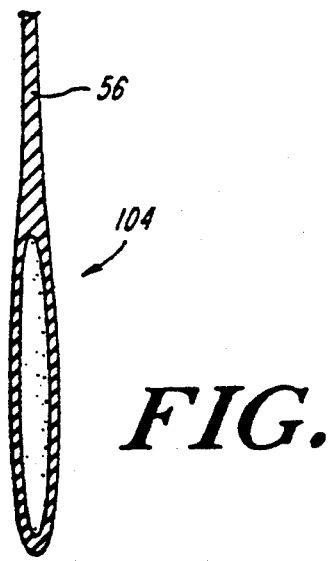
FIG. 6C is a schematic cross-sectional view of another encapsulation vehicle formed according to the invention.

The products can also take the form of 'tethered' cell capsules, that is, one or more individual cell compartments connected to a long polymeric tube, rod or string. In FIG. 6C, such a tethered cell capsule 104 is shown having a polymeric membrane 52 surrounding an encapsulated cell solution 54 with individual cells disposed therein. The cell capsule 104 further includes a long polymeric filament 56, or tether, which can be formed by interrupting the flow of the cell solution while maintaining flow of the casting solution.

The tethered vehicle illustrated in FIG. 6C may be manufactured according to the inventive method. For that vehicle 104, the steps of initiating extrusion of the casting solution, initiating delivery of the coagulant, then terminating delivery of the coagulant are performed substantially as for manufacturing other vehicles. However, unlike the other embodiments, following termination of delivery of the coagulant, extrusion of the casting solution continues for a period of time to make a tether 56. During this time, since the coagulant is not available to promote phase inversion, means should be provided to promote phase inversion of the extruded coating material which will form the tether (e.g., humidity, immersion, or coagulant bath). The longer the casting solution continues to extrude, the longer will be the resulting tether 56. The desired length of the tether 56 will vary in accordance with the target treatment site at which the capsule will be placed, as well as with physical limitations imposed by the material and apparatus used in manufacturing the vehicles.

The tether 56 also can be post-coated with a material (e.g., a polyurethane or the like) which imparts additional strength to the filament. Such tethered cell capsules can find a variety of applications, particularly when implanted in a subject for delivery of active factors. In use, the cell capsule can be located as close to the target region, or treatment site, (e.g., in the brain, peritoneal cavity or elsewhere) as desired, while the other end of the tether can be fixed at a convenient anchor point or disposal in a readily accessible location for retrieval.

Figure 6D:
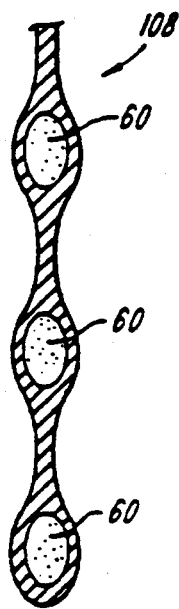
FIG. 6D is a schematic cross-sectional view of another encapsulation vehicle formed according to the invention.

In yet another form, and as illustrated in FIG. 6D, the encapsulation vehicle 108 may be a string of capsules 60, each capsule 60 containing an aliquot of biologically active materials separated by a length of polymer. This string of capsules 108 may be manufactured in accordance with the inventive method by alternating between initiating and terminating delivery of the coagulant, while the casting solution continuously extrudes.

Figure 6E:
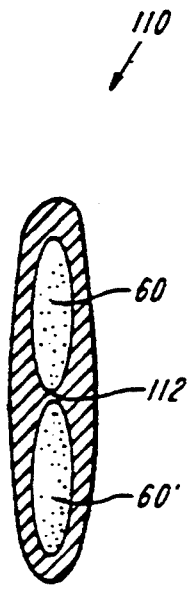
FIG. 6E is a schematic cross-sectional view of yet another encapsulation vehicle formed according to the invention.

Another variation in vehicle configuration is shown in FIG. 6E in which a vehicle 110 is constructed with two capsules 60, 60' located in close proximity to each other and separated by a thin, semipermeable intravehicular membrane 112.

Figure 6F:
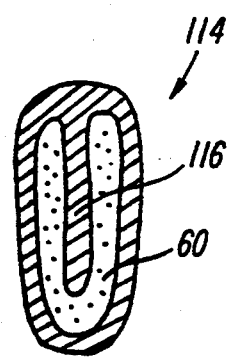
FIG. 6F is a schematic cross-sectional view of yet another encapsulation vehicle formed according to the invention.

Another variation in vehicle configuration is shown in FIG. 6F, in which a vehicle 114 is constructed having a solid inner core 116 and the cell chamber 60 is disposed between the inner core 116 and the outer membrane 118. An inner core (e.g. a coaxial rod) within the center chamber can be used to fill space and keep encapsulated cells located radially within the capsule. This allows the generation of capsules of increased cross sectional area. Normally cells in the center of large cross sectional area capsules are deprived of nutrients and oxygen. The presence of the center rod keeps cells from this unfavorable region of the capsule. Furthermore the center rod may in some cases serve as additional growth surface for encapsulated cells.

Capsules containing a coaxial rod can be produced by a simple modification of the system described above in connection with FIGS. 4A and 4B. The normal nozzle has an inner bore diameter of 0.72 mm with a 0.5 mm plunger. The plunger is usually allowed to extend only a short distance into the delivery channel (center bore). The inner diameter of the center bore was reduced to 0.69 mm. In addition the plunger was adjusted to move a considerable distance into the center bore during the down stroke. The reduction in bore diameter and increased traverse of the plunger into the center bore lead to a production of a vacuum when the plunger was withdrawn (up stroke). Capsules were extruded as normal (care was taken to produce a center bore flow high enough so the coaxial portion could be ejected from the center bore partially by coagulant flow and partially by plunger movement).

Figure 7:
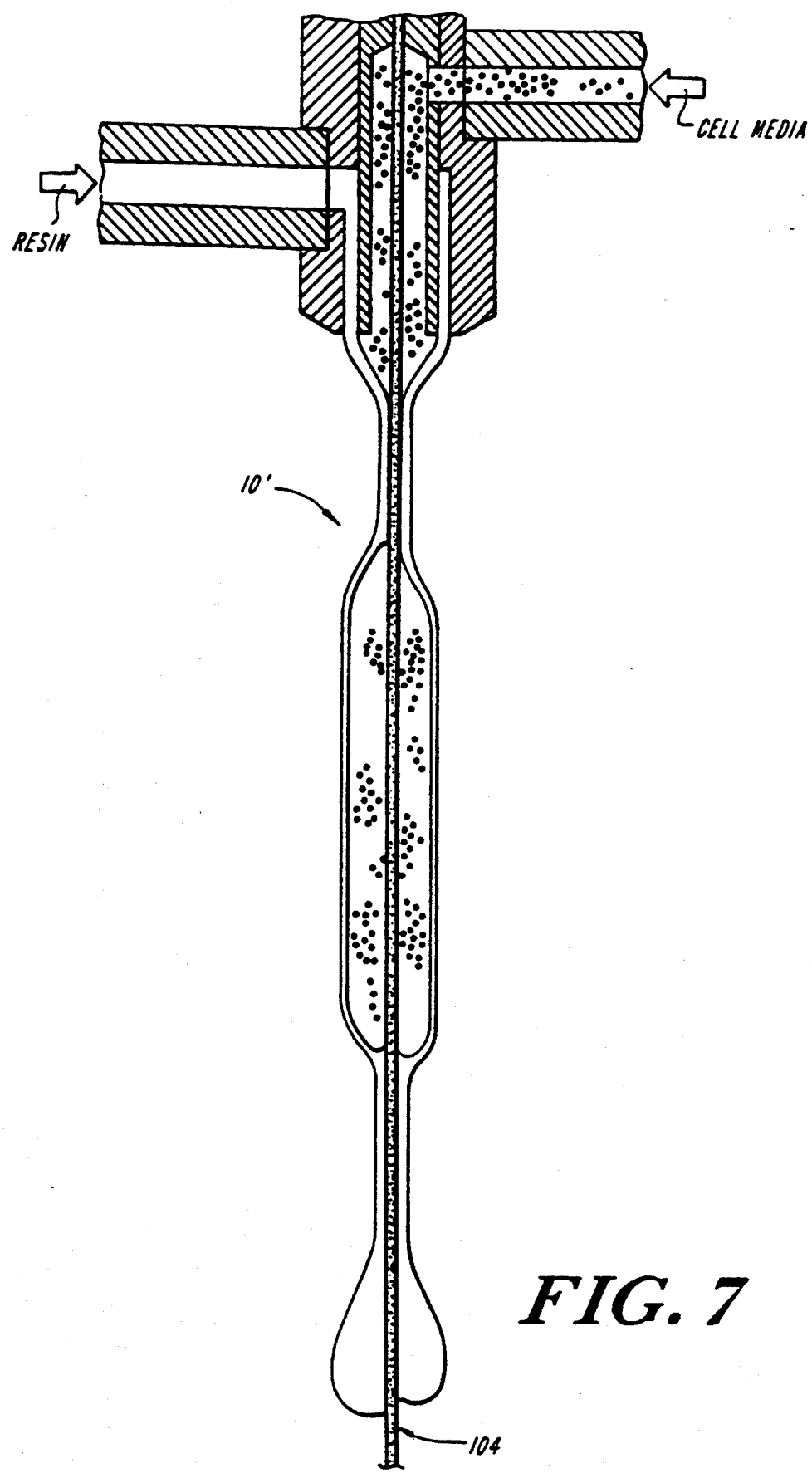
FIG. 7 is a longitudinal section view of a string vehicle used in practicing the present invention.

Yet another embodiment of the device 10' is shown in FIG. 7. In that embodiment, the device 10' includes a string of cell chambers 120, with a thread 104 captured along the length of the device. The thread is used to assist in formation of the device 10' during coextrusion of a polymer casting solution and a cell suspension solution. The thread 104 may be used to pull-start initial polymer feed through the extrusion system.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A method of integrally forming an elongated seamless capsule having a first end and a second end, the method comprising the sequential steps of:
   initiating extrusion of a casting solution through a first outer bore of a multiple annular extrusion port;
   subsequently initiating delivery of a coagulant to a second inner bore of the extrusion port to form a coextruded inner core and achieve a smooth first end of a seamless capsule, the coagulant comprising an aqueous solution containing biological material;
   terminating delivery of the coagulant; and
   subsequently terminating delivery of the casting solution such that essentially no extruded casting solution remains attached to the port to achieve a smooth second end of the seamless capsule, the coagulant with the biological material being contained within the seamless capsule;
   wherein the casting solution and the coagulant are selected so that coagulation of the casting solution occurs as the casting solution and the coagulant are extruded through the extrusion port.

2. The method of claim 1 wherein a smooth outer surface is formed on the capsule and autoinitiation is facilitated by extruding the casting solution through a non-porous bore.

3. The method of claim 2 wherein the non-porous bore is a glass bore.

4. The method of claim 1 wherein a step of terminating delivery of the coagulant is followed by a predetermined time delay before termination of the casting solution delivery to form an extended polymeric tether.

5. The method of claim 1 wherein before terminating delivery of the casting solution, delivery of the coagulant is repeatedly sequentially initiated and terminated to form a string of capsules.

6. The method of claim 1 wherein the casting solution is coagulated in an ambient environment external to the casting solution.

7. The method of claim 1 wherein the casting solution is coagulated in an aqueous environment external to the casting solution.

8. The method of claim 1 wherein the coagulant comprises a therapeutic factor.

9. The method of claim 1 wherein the coagulant comprises an aqueous suspension including cells that secrete a biologically active factor.

10. The method of claim 9 wherein the biologically active factor is a neurological factor.

11. The method of claim 10 wherein the neurological factor is a neurotransmitter.

12. The method of claim 9 wherein the biologically active factor is a hormone.

13. The method of claim 12 wherein the hormone is insulin or an active fragment or analog thereof.

14. The method of claim 1 wherein the coagulant comprises an aqueous cell suspension which includes an additive selected from the group consisting of a nutrient medium, an anchorage substrate material, and a combination thereof.

15. The method of claim 1 wherein the casting solution comprises a polymeric solution which includes an additive selected from the group consisting of a surfactant, an anti-inflammatory agent, an antioxidant, an angiogenic factor, and a combination thereof.

16. The method of claim 1 further comprising controlling the viscosity of the casting solution, such that upon coagulation the casting solution will form a capsule having a semipermeable membrane surrounding the coagulant comprising the biological material.

17. The method of claim 1 wherein the casting solution contains solvent and the method further comprises maintaining a pressure differential between the coagulant and the casting solution during co-extrusion to impede solvent diffusion from the casting solution into the coagulant.

18. The method of claim 1 wherein the subsequent initiation of delivery of the coagulant is within a range of between 10 milliseconds and about one second from the initiation of extrusion of the casting solution.

19. The method of claim 1 wherein the subsequent initiation of delivery of the coagulant occurs after a drop of casting solution is removed from the extrusion port and an optimal amount of casting solution remains at the extrusion port to form a smooth first end.

20. An elongated seamless capsule, having a first end and a second end, formed according to the following sequential steps:
  initiating extrusion of a casting solution through a first outer bore of a multiple annular extrusion port;
  subsequently initiating delivery of a coagulant to a second inner bore of the extrusion port to form a coextruded inner core and achieve a smooth first end of a seamless capsule, the coagulant comprising an aqueous solution containing biological material;
  terminating delivery of the coagulant; and
  subsequently terminating delivery of the casting solution such that essentially no extruded casting solution remains attached to the port to achieve a smooth second end of the seamless capsule, the coagulant with the biological material being contained within the seamless capsule;
  wherein the casting solution and the coagulant are selected so that coagulation of the casting solution occurs as the casting solution and the coagulant are extruded through the extrusion port.

21. The capsule of claim 20 further comprising a tether integral with and extending from the capsule.

22. The capsule of claim 20 wherein the biological material comprises cells which secrete a neurotransmitter.

23. The capsule of claim 20 further comprising a plurality of the fillable chambers, connected to each other by polymeric links.

24. The capsule of claim 20 wherein the capsule comprises at least two component layers of different porosity.

25. The capsule of claim 24 wherein the capsule comprises an inner porous layer having a molecular weight cutoff of about 40–60 kD.

26. The capsule of claim 24 wherein the capsule comprises an outer porous layer having a molecular weight cutoff of about 40–60 kD.

27. The capsule of claim 24 wherein the capsule comprises a porous inner skin layer having a molecular weight cutoff of about 40–60 kD, a porous outer skin layer having a molecular weight cutoff of about 40–60 kD and an intermediate layer of greater porosity.

28. The capsule of claim 20 wherein the capsule further comprises a solid inner core and said biological material is disposed between the inner core and capsule wall.

29. A method of integrally forming an elongated seamless capsule having a first end and a second end, the method comprising the sequential steps of:
  initiating extrusion of a casting solution through a first outer bore of a multiple annular extrusion port;
  subsequently initiating delivery of a coagulant to a second inner bore of the extrusion port to form a coextruded inner core and achieve a smooth first end of a seamless capsule, the coagulant comprising an aqueous solution containing biological material;
  maintaining the flow rate of the coagulant at a faster rate than the flow rate of the casting solution;
  terminating delivery of the coagulant; and
  subsequently terminating delivery of the casting solution such that essentially no extruded casting solution remains attached to the port to achieve a smooth second end of the seamless capsule, the coagulant with the biological material being contained within the seamless capsule;
  wherein the casting solution and the coagulant are selected so that coagulation of the casting solution occurs as the casting solution and the coagulant are extruded through the extrusion port.

30. A method of integrally forming an elongated seamless capsule having a first end and a second end comprising the sequential steps of:
  initiating extrusion of a casting solution containing a solvent through a first outer bore of a multiple annular extrusion port;
  subsequently initiating delivery of a coagulant to a second inner bore of the extrusion port to form a coextruded inner core and achieve a smooth first end of a seamless capsule, the coagulant comprising an aqueous solution containing biological material;
  maintaining a pressure differential between the coagulant and the casting solution during at least a portion of co-extrusion to impede solvent diffusion from the casting solution into the coagulant, and to cause coagulation of the casting solution as the casting solution and the coagulant are extruded through the extrusion port;
  terminating delivery of the coagulant; and
  subsequently terminating delivery of the casting solution such that essentially no extruded casting solution remains attached to the port to achieve a smooth second end of the seamless capsule, the coagulant with the biological material being contained within the seamless capsule.

31. A method of integrally forming an elongated seamless capsule having a first end and a second end, the method comprising the sequential steps of:

initiating extrusion of a casting solution through a first outer bore of a multiple annular extrusion port, the casting solution having a water-miscible solvent component;

subsequently initiating delivery of an aqueous coagulant, containing biological material, to a second inner bore of the extrusion port to form a coextruded inner core and achieve a smooth first end of a seamless capsule;

terminating delivery of the coagulant; and subsequently terminating delivery of the casting solution such that essentially no extruded casting solution remains attached to the port to achieve a smooth second end of the seamless capsule, the coagulant with the biological material being contained within the seamless capsule, wherein coagulation of the casting solution occurs as the casting solution and the coagulant are extruded through the extrusion port.

* * * * *